United States Patent
Yokoyama

(10) Patent No.: US 9,896,715 B2
(45) Date of Patent: Feb. 20, 2018

(54) METHOD FOR ANALYZING FORMYL GLYCINE RESIDUE

(71) Applicant: JCR PHARMACEUTICALS CO., LTD., Hyogo (JP)

(72) Inventor: Tetsuo Yokoyama, Hyogo (JP)

(73) Assignee: JCR PHARMACEUTICALS CO., LTD., Ashiya-Shi, Hyogo (JP)

( * ) Notice: Subject to any disclaimer, the term of this patent is extended or adjusted under 35 U.S.C. 154(b) by 790 days.

(21) Appl. No.: 14/366,533

(22) PCT Filed: Dec. 18, 2012

(86) PCT No.: PCT/JP2012/082734
§ 371 (c)(1),
(2) Date: Oct. 31, 2014

(87) PCT Pub. No.: WO2013/094579
PCT Pub. Date: Jun. 27, 2013

(65) Prior Publication Data
US 2015/0044715 A1 Feb. 12, 2015

(30) Foreign Application Priority Data
Dec. 20, 2011 (JP) .................. 2011-278560

(51) Int. Cl.
C12Q 1/44 (2006.01)
G01N 33/68 (2006.01)
B01D 15/32 (2006.01)
G01N 30/88 (2006.01)

(52) U.S. Cl.
CPC ............ *C12Q 1/44* (2013.01); *B01D 15/325* (2013.01); *G01N 33/6812* (2013.01); *G01N 33/6815* (2013.01); *G01N 2030/8831* (2013.01); *G01N 2333/916* (2013.01)

(58) Field of Classification Search
None
See application file for complete search history.

(56) References Cited

U.S. PATENT DOCUMENTS 5,932,211 A 8/1999 Wilson et al.
6,541,254 B1 4/2003 Wilson et al.

FOREIGN PATENT DOCUMENTS

| EP | 1311707 | 5/2003 |
|---|---|---|
| EP | 1850132 | 10/2007 |
| JP | 2003532900 | 11/2003 |
| JP | 2006510356 | 3/2006 |
| JP | 2006517412 | 7/2006 |
| JP | 2007519404 | 7/2007 |
| JP | 2007532882 | 11/2007 |
| WO | 200186306 | 11/2001 |
| WO | 2004043373 | 5/2004 |
| WO | 2004072275 | 8/2004 |
| WO | 2005073367 | 8/2005 |
| WO | 2005101017 | 10/2005 |

OTHER PUBLICATIONS

Dierks T. et al. Conversion of cysteine to formylglycine: A protein modification in the endoplasmic reticulum. 1997. PNAS. vol. 94. pp. 11963-11968.*
Wang S et al. Proteomics based on selecting and quantifying cysteine containing peptides by covalent chromatography. 2001. Journal of Chromatography A. 924. 345-357.*
Schmidt et al.: "A Novel Amino Acid Modification in Sulfatases That Is Defective in Multiple Sulfatase Deficiency"; Cell; 1995, vol. 82, pp. 271-278.
International search report for International application No. PCT/JP2012/082734, dated Mar. 26, 2013 (4 pages).
Dierks et al. "Multiple Sulfatase Deficiency Is Caused by Mutations in the Gene Encoding the Human Cα-Formylglycine Generating Enzyme", CELL, vol. 113, No. 4, p. 435-444, May 16, 2003, total 10 pages.

* cited by examiner

*Primary Examiner* — Paul J Holland
(74) *Attorney, Agent, or Firm* — Hamre, Schumann, Mueller & Larson, P.C.

(57) ABSTRACT

Disclosed is a method which enables semiquantitative or quantitative determination of the ratio between cysteine and formylglycine residues in a protein. The method includes (a) a step of labeling the protein (i) with a halogen-substituted carboxylic acid, (ii) with a halogen-substituted carboxylic acid amide, and (iii) with a halogen-substituted carboxylic acid and then with hydrazine, or with a halogen-substituted carboxylic acid and then by oximation, (b) a step of digesting each labeled protein to provide a corresponding mixture of peptide fragments, (c) a step of subjecting each mixture to reverse phase chromatography to separate the peptide fragments from each other to produce a chromatogram, (d) a step of comparing the produced chromatograms with each other to identify the peak corresponding to the peptide fragment that contained a cysteine residue and the peak corresponding to the peptide fragment that contained a formylglycine residue.

15 Claims, 1 Drawing Sheet

SEQUENCE LISTING

<160> NUMBER OF SEQ ID NOS: 1

<210> SEQ ID NO 1
<211> LENGTH: 28
<212> TYPE: PRT
<213> ORGANISM: Homo sapiens

```
<400> SEQUENCE: 1

Ser Pro Asn Ile Asp Gln Leu Ala Ser His Ser Leu Leu Phe Gln Asn
1               5                   10                  15

Ala Phe Ala Gln Gln Ala Val Cys Ala Pro Ser Arg
            20                  25
```

METHOD FOR ANALYZING FORMYL GLYCINE RESIDUE

TECHNICAL FIELD

The present invention relates to analysis of a protein, in more detail, to a method of analysis for a formylglycine residue generated by conversion of a cysteine residue in the peptide chain of a protein. In particular, the present invention relates to a method for determination of the ratio between formylglycine and cysteine residues in the peptide chain of an analyte protein, based on the peptide fragments obtained by enzymatic digestion of the protein.

BACKGROUND ART

Sulfatase (sulfuric ester hydrolase) has an activity to hydrolyze various biomolecules containing ester-linked sulfate groups, releasing the sulfate groups. In a human, at least nine types of sulfatases occur which differ in their substrate specificity. Each of these sulfatases contains a formylglycine residue (2-amino-3-oxopropionate residue) in its peptide chain (Non-patent Document 1). This formylglycine residue, which is one of the amino acid residues constituting the active center, is a residue generated by conversion of a certain cysteine residue originally present in the amino acid sequence of the sulfatase just after its translation. The formylglycine residue is hydrated and occurs in a gem-diol form in the catalytic reactions of sulfatase, and one of the two hydroxyl groups of the gem-diol is essential for the generation of an enzyme-sulfuric acid ester intermediate, and the other hydroxyl group is required for separation of a sulfate group. Therefore, the conversion of the cysteine residue to a formylglycine residue is essential for the sulfatase activity. In multiple sulfatase deficiency, which is a genetic disease caused by severe reduction of all sulfatase activities, there is no abnormality in the sulfatase gene itself, but the normal conversion of the cysteine residue to a formylglycine residue fails to take place, and as a result, sulfatase activities are lost or markedly reduced (Non-patent Document 1, Patent Document 1).

Thus, in quantitative determination of a sulfatase in a living body, measurement of mere its total amount is insufficient for quantitative evaluation of its enzyme activity, and thus it is necessary to determine the ratio at which the cysteine residue has been converted into a formylglycine residue in the sulfatase. The same is true of a recombinant sulfatase manufactured using recombinant DNA technology. As for a recombinant sulfatase, a method for production of arylsulfatase A has been reported, in which the cysteine residue has been converted into a formylglycine residue at a desired ratio (Patent Document 2). With an enzyme produced by this method, too, the ratio must be determined at which the cysteine residue has been converted into a formylglycine residue.

Iduronate 2-sulfatase (I2S) is one of sulfatases having an activity to hydrolyze sulfate ester bonds of heparan sulfate and dermatan sulfate, both belonging to the glycosaminoglycans. In order for I2S to exhibit its enzymatic activity, it is also necessary, like other sulfatases, that its predetermined cysteine residue located in the active center has been converted into a formylglycine residue.

Genetic deficiency of this enzyme leads to the development of Hunter syndrome (mucopolysaccharidosis type II), associated with such signs as skeletal abnormalities, caused by abnormal metabolism of heparan sulfate and dermatan sulfate and resulting accumulation of their partial degradation products in the tissues such as the liver and spleen. For patients with Hunter syndrome, enzyme replacement therapy is performed to supplement I2S. I2S employed in enzyme replacement therapy for Hunter syndrome has been produced as recombinant human I2S using CHO cells transformed with an expression vector with an incorporated human I2S gene. Various methods for producing recombinant human I2S using CHO cells have been reported (Patent Documents 3 and 4).

In order for a recombinant human I2S to exhibit its enzymatic activity, it is also necessary, like naturally occurring I2S, that the cysteine residue has been converted into a formylglycine residue. Thus, in quantitative determination of a recombinant human I2S, measurement of mere its total amount is insufficient for quantitative evaluation of its enzyme activity, and thus it is necessary to determine the ratio at which the cysteine residue has been converted into a formylglycine residue in the I2S.

N-acetylgalactosamine-4-sulfatase (ASB), also called arylsulfatase B, is one of sulfatases and has an activity to release sulfuric acid ions by hydrolyzing chondroitin-4-sulphate, dermatan sulfate and UDP-N-acetylgalactosamine-4-sulfate. In order for ASB to exhibit its enzymatic activity, it is also necessary, like other sulfatases, that its predetermined cysteine residue located in the active center has been converted into a formylglycine residue. Genetical deficiency of this enzyme would cause accumulation of dermatan sulfate and the like in the lysosomes of a wide range of tissues, which results in the development of Maroteaux-Lamy syndrome (mucopolys accharidosis type VI), which exhibits such symptoms as growth retardation, marked deformation of the spine and limbs, hepatosplenomegaly, and congenital cataract. For patients with Maroteaux-Lamy syndrome, enzyme replacement therapy is performed to supplement ASB. ASB used in enzyme replacement therapy of Maroteaux-Lamy syndrome has been produced as a recombinant human ASB using CHO cells transformed with an expression vector with an incorporated human ASB gene (Patent Document 5).

In order for a recombinant human ASB to exhibit its enzymatic activity, it is also necessary, like naturally occurring ASB, that the cysteine residue has been converted into a formylglycine residue. Thus, in quantitative determination of a recombinant human ASB, measurement of mere its total amount is insufficient for quantitative evaluation of its enzyme activity, and it is necessary to determine the ratio at which the cysteine residue has been converted into a formylglycine residue in the ABS.

In addition to Hunter syndrome and Maroteaux-Lamy syndrome, the diseases caused by deficiency of sulfatase include Morquio disease type A, and San Filippo syndrome A and D types, in which are found genetic deficiency of N acetylgalactosamine-6-sulfatase, heparan-N-sulfatase, and N-acetyl glucosamine-6-sulfate sulfatase, respectively. As for treatment of these diseases also, application of enzyme replacement therapy is conceivable employing enzymes produced using recombinant technology, in which, too, conversion of the cysteine residue to a formylglycine residue is essential in order for these enzymes produced using recombinant technology to exhibit their enzymatic activities. Thus, in quantitative determination of each of these enzymes, measurement of mere its total amount is insufficient, and it is necessary to determine the ratio at which the cysteine residue has been converted into a formylglycine residue in the enzymes.

As a method for determination of the amount of a sulfatase in which the particular cysteine residue originally present in the sulfatase is converted into a formylglycine residue, there is known a method comprising; digesting the sulfatase into peptide fragments by trypsin treatment, and then subjecting the peptide fragments to reverse phase column chromatography, and comparing, on the chromatogram thus produced, a peak corresponding to a peptide fragment containing the formylglycine residue with a peak corresponding to a peptide fragment containing the cysteine residue (Non-patent Document 1). This method does not allow one to identify, on a resulting chromatogram alone, the peak corresponding to a cysteine residue-containing peptide fragment or to a formylglycine residue-containing peptide fragment. According to this method, therefore, it is required to collect all the fractions corresponding to respective peaks, and then analyze the amino acid sequence of the peptide fragment contained in each of these fractions, one by one, to identify the aimed peptide fragments. Thus, it is very complicated to follow its procedure. And in the case of a protein made up of a long peptide chain, its treatment with trypsin gives an increased number of peptide fragments, and so an increased number of peaks are produced by their separation with reverse phase column chromatography. This, therefore, makes the procedure more complicated.

PRIOR ART DOCUMENTS

Patent Documents

Patent Document 1: JP 2006-617412
Patent Document 2: JP 2007-519404
Patent Document 3: U.S. Pat. No. 6,932,211
Patent Document 4: U.S. Pat. No. 6,641,254
Patent Document 5: JP 2006-610366

Non-Patent Documents

Non-patent Document 1: Schmidt B. et al., Cell, 82: 271-8 (1998).

SUMMARY OF INVENTION

The Problem to be Solved by the Invention

Against the above background, the objective of the present invention is to provide a method for determination of the ratio between cysteine and formylglycine residues in the peptide chain of a protein, either semiquantitatively or quantitatively.

Means to Solve the Problem

In a study directed to the above objective, the present inventor found that a peptide fragment which had contained a cysteine residue when in the original protein as well as a peptide fragment which had contained a formylglycine residue when in the original protein, can be easily identified, and thus that the ratio between the cysteine residue and the formylglycine residue generated by conversion of a cysteine residue in the peptide chain of the analyte protein, can be determined, either semiquantitatively or quantitatively: by preparing a differently labeled protein by labeling the cysteine residue of a protein with iodoacetic acid, with iodoacetamide, or with iodoacetic acid or iodoacetamide and also with a hydrazine compound or a hydroxylamine compound (herein referred to as "hydrazine-labeling" or "oximation-labeling", respectively); and then digesting each of them to a peptide fragment mixture; subjecting each of the peptide fragment mixtures to reverse phase column chromatography; and comparing between the chromatograms thus produced. The present invention was completed based on this finding. Thus, the present invention provides what follows.

1. A method of analysis for a formylglycine residue and a cysteine residue in the amino acid residues that makes up an analyte protein comprising,
   (a) a step of converting the protein respectively into
      (i) a halogen-substituted carboxylic acid-labeled protein by labeling the protein with a halogen-substituted carboxylic acid,
      (ii) a halogen-substituted carboxylic acid amide-labeled protein by labeling the protein with a halogen-substituted carboxylic acid amide, and
      (iii) a halogen-substituted carboxylic acid-hydrazine-labeled protein or a halogen-substituted carboxylic acid-oximation-labeled protein by labeling the protein with a halogen-substituted carboxylic acid and then with hydrazine or by labeling with halogen-substituted carboxylic acid and then by oximation,
   (b) a step of digesting each of the labeled proteins to provide a corresponding mixture of peptide fragments,
   (c) a step of subjecting each mixture of peptide fragments to reverse phase chromatography to separate the peptide fragments from each other while monitoring the separated fragments with absorptiometer, producing a chromatogram of the mixture of peptide fragments,
   (d) a step of comparing the produced chromatograms with each other to identify, on the chromatograms, the peak corresponding to a peptide fragment which contained a cysteine residue when in the analyte protein and the peak corresponding to a peptide fragment which contained a formylglycine residue when in the analyte protein.

2. A method of analysis for a formylglycine residue and a cysteine residue in the amino acid residues that makes us an analyte protein comprising:
   (a) a step of converting the protein respectively into
      (i) a halogen-substituted carboxylic acid-labeled protein by labeling the protein with a halogen-substituted carboxylic acid,
      (ii) a halogen-substituted carboxylic acid amide-labeled protein by labeling the protein with a halogen-substituted carboxylic acid amide, and
      (iii) a halogen-substituted carboxylic acid amide-hydrazine-labeled protein or a halogen-substituted carboxylic acid amide-oximation-labeled protein by labeling the protein with a halogen-substituted carboxylic acid amide and then with hydrazine or by labeling the protein with a halogen-substituted carboxylic acid amide and then by oximation,
   (b) a step of digesting each of the labeled proteins to provide a corresponding mixture of peptide fragments,
   (c) a step of subjecting each mixture of peptide fragments to reverse phase chromatography to separate the peptide fragments from each other while monitoring the separated fragments with an absorptiometer to produce a chromatogram of the mixture of peptide fragments.
   (d) a step of comparing the produced chromatograms with each other to identify, on the chromatograms, the peak corresponding to a peptide fragment which contained a cysteine residue when in the analyte protein and the peak corresponding to the peptide fragment that contained a formylglycine residue when in the analyte protein.

3. The method according to 1 or 2 above, wherein the sulfhydryl group of the cysteine residue in the analyte protein is alkylated with the halogen-substituted carboxylic acid or the halogen-substituted carboxylic acid amide in the labeling with halogen-substituted carboxylic acid or the labeling with halogen-substituted carboxylic acid amide, respectively.

4. The method according to 3 above, wherein the halogen-substituted carboxylic acid is a halogen-substituted monocarboxylic acid represented by the following formula (I),

[Chem. 1]

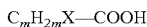  (I)

wherein X denotes halogen, and m denotes an integer of 1 to 5,
and the halogen-substituted carboxylic acid amide is a halogen-substituted monocarboxylic acid amide represented by the following formula (II),

[Chem. 2]

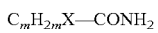  (II)

wherein X denotes halogen, and m denotes an integer of 1 to 5.

5. The method according to 4 above, wherein m is an integer of 1 to 3 in formula (I) and formula (II).

6. The method according to 4 or 5 above, wherein the halogen is chlorine or iodine in formula (I) and formula (II).

7. The method according to 3 above, wherein the halogen-substituted carboxylic acid is an iodo-substituted monocarboxylic acid or a chloro-substituted monocarboxylic acid; and the halogen-substituted carboxylic acid amide is an iodo-substituted monocarboxylic acid amide or a chloro-substituted monocarboxylic acid.

8. The method according to 7 above, wherein the halogen-substituted monocarboxylic acid is one selected from the group consisting of iodoacetic acid, 2-iodopropionic acid, 3-iodopropionic acid, and chloroacetic acid, and the halogen-substituted carboxylic acid amide is one selected from the group consisting of iodoacetamide, 2-iodopropionic acid amide, 3-iodopropionic acid amide, and chloroacetamide.

9. The method according to 7 above, wherein the halogen-substituted monocarboxylic acid is iodoacetic acid and the halogen-substituted carboxylic acid amide is iodoacetamide.

10. The method according to 7 above, wherein the halogen-substituted monocarboxylic acid is 3-iodo-propionic acid and the halogen-substituted carboxylic acid amide is iodoacetamide.

11. The method according to one of 1 to 10 above, wherein the labeling with hydrazine is performed using a hydrazine compound or a salt thereof that forms a hydrazone with the carbonyl group of a formylglycine residue.

12. The method according to 11 above, wherein the hydrazine compound or the salt thereof is a 2,4-dinitrophenylhydrazine or a salt thereof.

13. The method according to one of 1 to 10 above, wherein the labeling by oximation is performed using a hydroxyl amine compound or a salt thereof that forms an oxime group with the carbonyl group of a formylglycine residue.

14. The method according to 13 above, wherein the hydroxylamine compound or the salt thereof is O-4-nitrobenzyl hydroxylamine or a salt thereof.

15. The method according to one of 1 to 14 above, further comprising a step for determining, on the chromatogram, the ratio of the area of the peak corresponding to the peptide fragment that contained a cysteine residue when in the analyte protein and the area of the peak corresponding to the peptide fragment that contained a formylglycine residue when in the analyte protein.

16. The method according to one of 1 to 15 above, wherein the analyte protein is a human sulfuric ester hydrolase.

17. The method according to 16 above, wherein the sulfuric ester hydrolase is selected from the group consisting of iduronate-2-sulfatase, N-acetylgalactosamine-4-sulfatase, N-acetylgalactosamine-6-sulfatase, heparan-N-sulfatase, and N-acetyl glucosamine-6-sulphate sulfatase.

18. The method according to 17 above, wherein the sulfuric ester hydrolase is iduronate-2-sulfatase.

19. The method according to one of 16 to 18 above, wherein the cysteine residue is that cysteine residue which must have been converted into a formylglycine residue in order for the sulfuric ester hydrolase to exhibit its enzymatic activity, and the formylglycine residue is that formylglycine residue which has been generated by conversion of the cysteine residue.

20. The method according to 19 above, wherein the sulfuric ester hydrolase is iduronate-2-sulfatase, and the cysteine residue and the formylglycine residue are those located at position 59 from the N-terminus of the mature iduronate-2-sulfatase.

21. The method according to 20 above, wherein the iduronate-2-sulfatase is a recombinant iduronate-2-sulfatase.

Effects of Invention

The present invention enables one to analyze an analyte protein, either semiquantitatively or quantitatively, for the ratio between its cysteine residue and its formylglycine residue generated by conversion of a cysteine residue, in the peptide chain of the protein molecules. Thus, the present invention enables one to determine, either semiquantitatively or quantitatively, the proportion of active enzyme molecules in an analyte enzyme, such as an enzyme which, like sulfatases, requires for exhibiting its activity that a certain cysteine residue located at its active center has been converted into a formylglycine residue.

Figure 1:
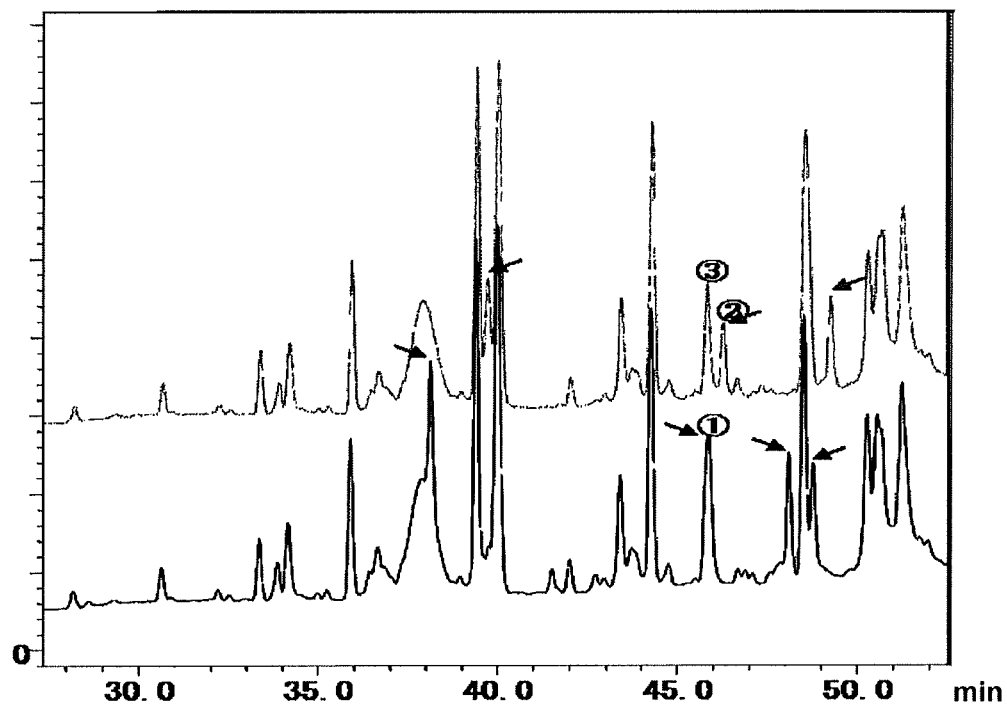
FIG. 1 shows chromatograms obtained as a result of analysis by reverse phase column chromatography of mixtures of peptide fragments prepared by trypsin digestion of iodoacetic acid-labeled rhI2S or iodoacetamide-labeled rhI2S, respectively aligned, the one upper and the other lower, with their elution time matched with each other. The upper of the chromatogram shows the result of analysis of iodoacetic acid-labelled rhI2S, and the lower of iodoacetamide-labelled rhI2S. The vertical axis represents absorbance (215 nm), and the horizontal axis the elution time. The arrows indicate the peaks of peptide fragments which had contained cysteine residues when in the analyte protein. Peaks (1) and (2) correspond to peptide fragments which had contained Cys59 when in the analyte protein, and peak (3) corresponds to a peptide fragment which had contained FGly59 when in the analyte protein.

The upper of the chromatograms shows the result of analysis of iodoacetic acid-labeled rhI2S, and the lower of iodoacetic acid-DNPH-labeled rhI2S. The vertical axis represents absorbance (215 nm), and the horizontal axis the elution time. Peak (3) corresponds to peptide fragment which had contained FGly59 when in the analyte protein, and peak (2) corresponds to a peptide fragment which had contained Cys59 when in the protein.

DESCRIPTION OF EMBODIMENTS

Conversion of a cysteine residue to a formylglycine residue in the peptide chain of a protein is represented by the following formula (1).

[Chem. 3]

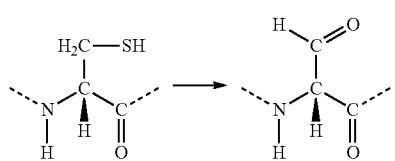

(1)

In the present invention, the reaction utilized to label a protein with a halogen-substituted carboxylic acid (halogen-substituted carboxylic acid-labeling reaction) is an alkylation reaction in which the sulfhydryl group of a cysteine residue is alkylated with a halogen-substituted carboxylic acid, and is exemplified by the reaction of labeling a protein using iodoacetic acid (iodoacetic acid-labeling reaction) as represented by the following formula (2), and the reaction product is herein referred to as "halogen-substituted carboxylic acid-labeled protein". When the protein labeled using this reaction is an enzyme, especially a lysosomal enzyme, more especially iduronate-2-sulfatase (I2S), and still more especially a recombinant human iduronate-2-sulfatase (rhI2S), the resulting product is herein referred to as "halogen-substituted carboxylic acid-labeled enzyme", especially "halogen-substituted carboxylic acid-labeled lysosomal enzyme", more especially "halogen-substituted carboxylic acid-labeled I2S", and still more especially "halogen-substituted carboxylic acid-labeled rhI2S", respectively, in the present specification. Further, a cysteine residue alkylated with a halogen-substituted carboxylic acid in a halogen-substituted carboxylic acid-labeled enzyme or its fragments, is herein referred to as "halogen-substituted carboxylic acid-labeled cysteine residue", and the moiety modified with a halogen-substituted carboxylic acid in a halogen-substituted carboxylic acid-labeled cysteine residue is referred to as "halogen-substituted carboxylic acid-labeled residue".

In the present invention, when the halogen-substituted carboxylic acid used for labeling a protein is iodoacetic acid, the product produced by the reaction [iodoacetic acid-labeling reaction represented by the following formula (2)] is herein referred to as "iodoacetic acid-labeled protein". When the protein labeled by this reaction is an enzyme, especially a lysosomal enzyme, more especially iduronate-2-sulfatase (I2S), and still more especially a recombinant human iduronate-2-sulfatase (rhI2S), the resulting product is herein referred to as "iodoacetic acid-labeled enzyme", especially "iodoacetic acid labeled-lysosomal enzyme", more especially "iodoacetic acid-labeled I2S", and still more especially "iodoacetic acid-labeled rhI2S", respectively. Further, a cysteine residue alkylated with iodoacetic acid in an iodoacetic acid-labeled enzyme or its fragments, is referred to as "iodoacetic acid-labeled cysteine residue", and the moiety modified with iodoacetic acid in the iodoacetic acid-labeled cysteine residue is referred to as "iodoacetic acid-labeled residue".

Products produced by labeling with other halogen-substituted carboxylic acids than iodoacetic acid, are referred to in the same manner as the product labeled using the iodoacetic acid-labeling reaction.

[Chem. 4]

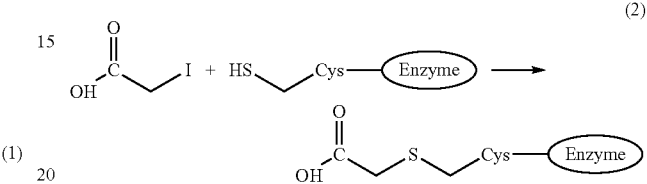

(2)

In the present invention, any halogen-substituted carboxylic acid amides may be employed without particular limitation as far as they can alkylate the sulfhydryl group of a cysteine residue of a protein, though preferred are those represented by the general formula (I) (in the formula, X denotes halogen, m denotes an integer of 1 to 5), and are those in which a hydrogen atom in the hydrocarbon chain of acetic acid, propionic acid, butyric acid, valeric acid, or caproic acid is substituted by a halogen, and more preferred are those in which a hydrogen atom in the hydrocarbon chain of acetic acid, propionic acid, or butyric acid is substituted by a halogen, and particularly preferred are those in which a hydrogen atom in the hydrocarbon chain of acetic acid or propionic acid is substituted by halogen. Further, in the above general formula (I), halogen is preferably iodine, chlorine, or bromine, and particularly preferably, iodine or chlorine. Preferable halogen-substituted carboxylic acids include iodoacetic acid, 2-iodopropionic acid (2-iodine propanoic acid), 3-iodopropionic acid (3-iodine propanoic acid), and chloroacetic acid, and more preferable are iodoacetic acid and 3-iodopropionic acid.

In the present invention, the reaction utilized to label a protein with a halogen-substituted carboxylic acid amide (halogen-substituted carboxylic acid amide-labeling reaction) is an alkylation reaction in which the sulfhydryl group of a cysteine residue is alkylated with a halogen-substituted carboxylic acid amide, exemplified by the reaction for labeling a protein with iodoacetic acid amide (iodoacetic acid amide-labeling reaction) as represented by the following formula (3), and the reaction product is referred to as "halogen-substituted carboxylic acid amide-labeled protein" When the protein labeled using this reaction is an enzyme, especially a lysosomal enzyme, more especially iduronate-2-sulfatase (I2S), and still more especially a recombinant human iduronate-2-sulfatase (rhI2S), the resulting product is referred to as "halogen-substituted carboxylic acid amide-labeled enzyme", especially "halogen-substituted carboxylic acid amide-labeled lysosomal enzyme", more especially "halogen-substituted carboxylic acid amide-labeled I2S", and still more especially "halogen-substituted carboxylic acid amide-labeled rh I2S", respectively. Further, a cysteine residue alkylated with a halogen-substituted carboxylic acid amide in a halogen-substituted carboxylic acid amide-labeled enzyme or its fragments, is referred to as "halogen-substituted carboxylic acid amide-labeled cysteine residue", and the moiety modified with the halogen-substituted carboxylic acid amide in the halogen-substituted carboxylic acid amide-labeled cysteine residue is referred to as "halogen-substituted carboxylic acid amide-labeled residue".

In the present invention, when the halogen-substituted carboxylic acid amide used for labeling a protein is iodoacetamide, the product produced by the reaction [iodoacetamide-labeling reaction represented by the following formula (3)] is referred to as "iodoacetamide-labeled protein". When the protein labeled by this reaction is an enzyme, especially a lysosomal enzyme, more especially iduronate-2-sulfatase (I2S), and still more especially a recombinant human iduronate-2-sulfatase (rhI2S), the resulting product is referred to as "iodoacetamide-labeled enzyme", especially "iodoacetamide-labeled lysosomal enzyme", more especially "iodoacetamide-labeled I2S", and still more especially "iodoacetamide-labeled rhI2S", respectively. Furthermore, a cysteine residue alkylated with iodoacetamide in an iodoacetamide-labeled enzyme or its fragment, is referred to as "iodoacetamide-labeled cysteine residue", and the moiety modified with iodoacetamide in the iodoacetamide-labeled cysteine residue is referred to as "iodoacetamide-labeled residue".

Products which are labeled with other halogen-substituted carboxylic acid amides than iodoacetamide also are referred to in the same manner as the products labeled through the iodoacetamide-labeling reaction.

[Chem. 5]

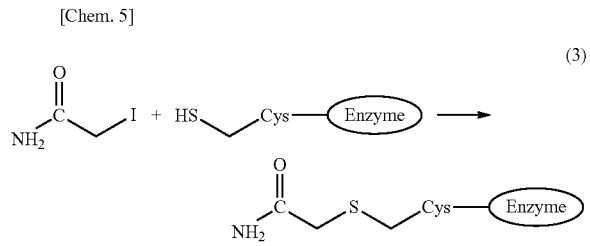

(3)

In the present invention, any halogen-substituted carboxylic acid amides may be employed without particular limitation as far as they can alkylate the sulfhydryl groups of a cysteine residue of a protein, though preferred are those represented by the general formula (II) (in the formula, X denotes halogen, m denotes an integer of 1 to 5), and are those in which a hydrogen atom in the hydrocarbon chain of acetic acid amide (acetamide), propionic acid amide, butyric acid amide, valeric acid amide or caproic acid amide is substituted by halogen, and more preferred are those in which a hydrogen atom in the hydrocarbon chain of acetic acid amide, propionic acid amide and butyric acid amide is substituted by halogen, and particularly preferred are those in which a hydrogen atom in the hydrocarbon chain of acetic acid amide and propionic acid amide is substituted with halogen. Further, in the general formula above, halogen is preferably iodine, chlorine, or bromine, and particularly preferably iodine or chlorine. Preferable halogen-substituted carboxylic acid amides include iodoacetic acid amide, 2-iodopropionic acid amide (2-iodine propanoic acid amide), 3-iodopropionic acid amide (3-iodine propanoic acid amide), and chloroacetic acid amide, and more preferable are iodoacetic acid amide or 3-iodopropionic acid amide.

In the present invention, the reaction utilized to label a formylglycine residue in a protein with a hydrazine compound or a salt thereof (hydrazine-labeling reaction) is a reaction in which a hydrazone is produced from the carbonyl group of a formylglycine residue and a hydrazine compound, and the resulting product is referred to as "hydrazine-labeled protein". When the protein labeled using this reaction is a halogen-substituted carboxylic acid-labeled protein, especially a halogen-substituted carboxylic acid-labeled lysosomal enzyme, more especially halogen-substituted carboxylic acid-labeled I2S, and still more especially a halogen-substituted carboxylic acid-labeled rhI2S, the resulting product is referred to as "halogen-substituted carboxylic acid-hydrazine-labeled protein", especially "halogen-substituted carboxylic acid-hydrazine-labeled lysosomal enzyme", more especially "halogen-substituted carboxylic acid-hydrazine-labeled I2S", and still more especially "halogen-substituted carboxylic acid-labeled hydrazine", respectively.

Furthermore, when the protein labeled using this reaction is an iodoacetic acid-labeled protein, especially an iodoacetic acid-labeled lysosomal enzyme, more especially iodoacetic acid-labeled I2S, and still more especially iodoacetic acid-labeled rhI2S, the resulting product is referred to as "iodoacetic acid-hydrazine-labeled protein", especially "iodoacetic acid-hydrazine-labeled lysosomal enzyme", more especially "iodoacetic acid-hydrazine-labeled I2S", and still more especially "iodoacetic acid-labeled hydrazine", respectively.

When the halogen-substituted carboxylic acid-labeled protein is other halogen-substituted carboxylic acid-labeled protein than iodoacetic acid-labeled protein, the product produced from it using the hydrazine-labeling reaction is also referred in the same manner as the product which is produced by hydrazine-labeling of the above iodoacetic acid-labeled protein.

In the present invention, any hydrazine compounds or salts thereof may be employed without particular limitation as far as they can form a hydrazone with the carbonyl group of a formylglycine residue in a protein, though preferred is 2,4-dinitrophenyl hydrazine or a salt thereof, in particular, 2,4-dinitrophenylhydrazine hydrochloride.

The following formula represents the reaction in which the carbonyl group of a formylglycine residue is labeled with 2,4-dinitrophenylhydrazine hydrochloride, one of hydrazine compounds (DNPH-labeling reaction). The product is referred to as "DNPH-labeled protein", and when the protein labeled according to this reaction is an iodoacetic acid-labeled protein, especially an iodoacetic acid-labeled enzyme, more especially an iodoacetic acid-labeled lysosomal enzyme, still more especially an iodoacetic acid-labeled I2S, and most especially iodoacetic acid-labeled rhI2S, the resulting product is referred to as "iodoacetic acid-DNPH-labeled protein", especially "iodoacetic acid-DNPH-labeled enzyme", more especially "iodoacetic acid-DNPH-labeled lysosomal enzyme", still more especially "iodoacetic acid-DNPH-labeled I2S", and most especially "iodoacetic acid-DNPH-labeled rhI2S", respectively.

[Chem. 6]

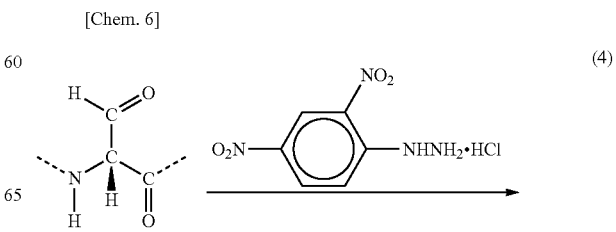

(4)

-continued

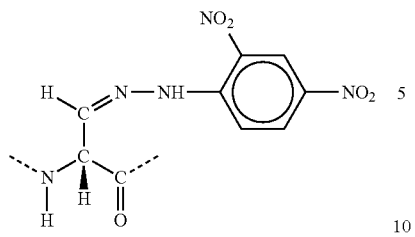

In the present invention, instead of a halogen-substituted carboxylic acid-labeled protein, a halogen-substituted carboxylic acid amide-labeled protein may also be labeled with hydrazine. Its reaction with 2,4-dinitrophenylhydrazine (DNPH) used as a hydrazine compound, is also as shown in the formula above. When the halogen-substituted carboxylic acid amide is iodoacetamide, the product produced by the hydrazine-labeling reaction using DNPH is referred to as "iodoacetamide-DNPH-labeled protein". When the iodoacetamide-labeled protein which is labeled by this reaction is, in particular, an iodoacetamide-labeled enzyme, especially an iodoacetamide-labeled lysosomal enzyme, more especially an iodoacetamide-labeled I2S, and still more especially an iodoacetamide-labeled rhI2S, the resulting product is referred to as "iodoacetamide-DNPH-labeled enzyme", especially "iodoacetamide-DNPH-labeled lysosomal enzyme", more especially "iodoacetamide-DNPH-labeled I2S", and still more especially "iodoacetamide-DNPH—labeled rhI2S", respectively.

In the present invention, instead of using a hydrazine compound such as 2,4-dinitrophenylhydrazine, a protein may be labeled using a compound that can form an oxime group (including herein those which are esterified at the hydroxyl moiety) by the reaction with the carbonyl group of a formylglycine residue, especially hydroxylamine compounds. Labeling by this reaction is referred to as oximation-labeling, and the resulting product is called "oximation-labeled protein." When the protein labeled by this reaction is especially an iodoacetic acid-labeled protein, more especially an iodoacetic acid-labeled-enzyme, still more especially an iodoacetic acid-labeled lysosomal enzyme, even more especially an iodoacetic acid-labeled I2S, and most especially an iodoacetic acid-labeled rhI2S, the resulting product is referred to as "iodoacetic acid-oximation-labeled protein", "iodoacetic acid-oximation-labeled lysosomal enzyme", "iodoacetic acid-oximation-labeled I2S", and "iodoacetic acid-oximation-labeled rhI2S".

Further, when the protein labeled by this reaction is an iodoacetamide-labeled protein, especially an iodoacetamide-labeled enzyme, more especially an iodoacetamide-labeled lysosomal enzyme, more especially an iodoacetamide-labeled I2S, and most especially an iodoacetamide-labeled rhI2S, the resulting product is referred to as "iodoacetamide-oximation-labeled protein", especially "iodoacetamide-oximation-labeled-enzyme", still more especially "iodoacetamide-oximation-labeled-lysosomal enzyme", still more especially "iodoacetamide-oximation-labeled I2S", and most especially "iodoacetamide-oximation-labeled rhI2S", respectively.

In this specification, the oxime group is represented by the following formula (5), and the hydroxylamine compound is represented by the following formula (6).

[Chem. 7]

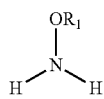

(5)

In formula (5), $R_1$ is selected from hydrogen, linear or branched alkyl, benzyl, aryl, linear or branched-alkenyl, alicyclic (a group consisting of alicyclic compound radical), or from combinations or derivatives thereof; the number of carbon atoms of the alkyl group is preferably 1 to 20, more preferably 1 to 12, still more preferably 1 to 6, and particularly preferably 1 to 3; the benzyl group may have a substituent on the benzene ring thereof and the substituent may be nitro; the number of carbon atoms of the alkenyl group is preferably 2 to 20, more preferably 2 to 12, still more preferably 1 to 6, and particularly preferably 2 to 3, and, the alkenyl group is an allyl group, for example; the number of carbon atoms of the aryl group is preferably 6 to 10; the number of carbon atoms of the alicyclic group is preferably 4 to 12, more preferably 4 to 10, and still more preferably 4 to 6.

[Chem. 8]

(6)

$$\underset{H}{\overset{OR_1}{N}}\underset{H}{}$$

In formula (6), $R_1$ is as defined above.

Further, the following formula (7) shows an example of oximation-labeling, i.e., a reaction wherein the carbonyl group of a formylglycine residue is labeled with O-4-nitrobenzyl hydroxylamine hydrochloride.

[Chem. 9]

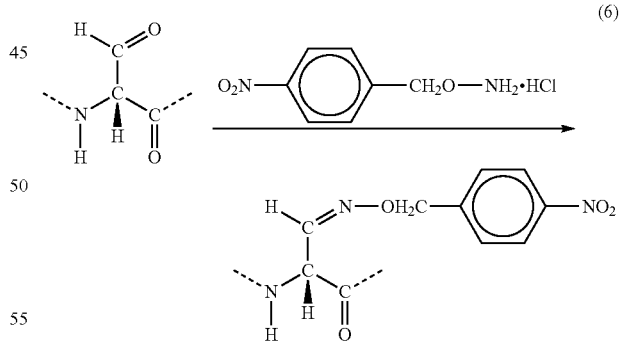

(6)

Under acidic conditions, such as in a trifluoroacetic acid aqueous solution, a residue labeled with a halogen-substituted carboxylic acid (e.g., iodoacetic acid-labeled residue) tends to have a lower charge and a higher hydrophobicity than a halogen-substituted carboxylic acid amide-labeled residue (e.g., iodoacetamide-labeled residue). Therefore, a protein (or its fragment) labeled with a halogen-substituted carboxylic acid and the same protein labeled with a halogen-substituted carboxylic acid amide, will differ in their elution time when subjected to reverse phase column chromatography under an acidic condition, and the protein (or its fragment) labeled with a halogen-substituted carboxylic acid will take a longer time to be eluted, as a general tendency.

For example, when a protein labeled with iodoacetic acid and the same protein labeled with iodoacetamide are compared after their decomposition into peptide fragments and subjection to reverse phase column chromatography under an acidic condition to obtain corresponding chromatograms, peptide fragments containing no cysteine residue, a residue which can be labeled either with iodoacetic acid or iodoacetamide, exhibit identical elution patterns with each other. On the other hand the elution patterns of peptide fragments containing a cysteine residue, a residue which can be labeled either with iodoacetic acid or iodoacetamide, differ from each other. Thus, the peaks corresponding to peptide fragments containing a cysteine residue can be easily identified on the chromatograms. As a general tendency, it takes a longer time for peptide fragments labeled with iodoacetic acid to be eluted.

In the present invention, when labeling a protein either with a halogen-substituted carboxylic acid (e.g., iodoacetic acid-labeled) or a halogen-substituted carboxylic acid amide (e.g., iodoacetamide-labeled), the protein is pretreated in either case. This pre-treatment, which is performed to label all the cysteine residues contained in the peptide chains of the protein, consists of two steps. The first step is a step to destroy the higher-order structure of the protein using a protein denaturant. The second step is a step to reduce disulfide bonds into cysteine residues with a reducing agent. Through in these steps, three-dimensional structure of the protein is destroyed and disulfide bonds reduced, all the cysteine residues present in the peptide chains are exposed in a state at which they are available for labeling. Though there is no particular limitation as to protein denaturants used in the first step as long as they can destroy the higher order structure of proteins and do not inhibit the labeling reaction, guanidine or hydrochloride salt thereof is preferred. Reducing agents to be used in the second step, though there are no particular limitation as to them as long as they can reduce disulfide bonds in the protein and do not hinder the labeling reaction, are preferably dithiothreitol and 2-mercaptoethanol, and more preferably dithiothreitol.

In the present invention, it is desirable that the protein labeled with halogen-substituted carboxylic acid (e.g., iodoacetic acid-labeled) or labeled with halogen-substituted carboxylic acid amide (e.g., iodoacetamide-labeled) is purified, following the labeling reaction, by gel filtration column chromatography, to reduce noises in the result of analysis.

In the present invention, when labeling a protein with hydrazine (such as with DNPH) or by oximation, it is preferable that the protein is first subjected to halogen-substituted carboxylic acid labeling (e.g. iodoacetic acid-labeling), or halogen-substituted carboxylic acid amide labeling (e.g. iodoacetamide-labeling), and then is subjected to hydrazine-labeling or oximation-labeling, though it is also possible to carry out hydrazine-labeling or oximation-labeling first, and then halogen-substituted carboxylic acid-labeling or halogen-substituted carboxylic acid amide-labeling.

In the present invention, a protein labeled with a halogen-substituted carboxylic acid (e.g. iodoacetic acid-labeling), halogen-substituted carboxylic acid amide (e.g. iodoacetamide-labeling), hydrazine-labeling, or by oximation-labeling is decomposed into peptide fragments using a method which allows cutting of the peptide bond of the protein, at specific positions selectively or preferentially. As such methods, there are enzymatic methods in which a protein is decomposed using a proteolytic enzyme (peptidase) and chemical methods in which a protein is decomposed by cyanogen bromide or the like without using a peptidase. Suitable peptidases to be used in an enzymatic method include trypsin, chymotrypsin, lysyl endopeptidase, glutamine endopeptidase, peptidyl-Asp metalloendopeptidase, and the like, among which trypsin is particularly preferred. As the chemical method, preferred is a method to decompose a protein using cyanogen bromide, 2-nitro-5-thiocyanobenzoic acid, or o-iodosobenzoic acid.

Peptide fragments obtained by the above method can be separated into respective molecular species by reverse phase column chromatography. Under acidic conditions, e.g., in a trifluoroacetic acid aqueous solution, an iodoacetic acid-labeled residue has a lower tendency to become electrically charged and is more hydrophobic than iodoacetamide-labeled residue. Therefore when subjected to reverse phase column chromatography under acidic conditions, peptide fragments labeled with iodoacetic acid and those labeled with iodoacetamide will differ in their elution time when subjected to reverse phase column chromatography under an acidic condition, with peptide fragments labeled with iodoacetic acid taking a longer time to be eluted than those labeled with iodoacetamide, as a general tendency. Therefore, it is possible to easily identify a peak corresponding to a peptide fragment which contained a cysteine residue when in the analyte protein, by analyzing the peptide fragments of the iodoacetic acid-labeled protein and the iodoacetamide-labeled protein, respectively, using reverse phase column chromatography under an acidic condition, and then comparing their chromatograms. This is because the positions of respective peaks corresponding to peptide fragments which contained no cysteine residue when in the analyte protein will match between both chromatograms, whereas the positions of the peak corresponding to a peptide fragment which contained a cysteine residue when in the analyte protein will differ between both chromatograms.

Furthermore, by analyzing the protein labeled with hydrazine or by oximation in the same manner as described above, it is possible to identify the peaks corresponding to peptides which contained a formylglycine residue. This is because when a hydrazine-labeled or oximation-labeled protein and the non-labeled protein are respectively analyzed and compared on their chromatograms, the peaks corresponding to peptide fragments which contained a formylglycine residue when in the analyte protein will appear at different positions in accordance with whether the protein was labeled or not, since a formylglycine residue undergoes hydrazine-labeling or oximation-labeling.

Thus, according to the present invention, by combinations of respective labeling of a protein using a halogen-substituted carboxylic acid (e.g., iodoacetic acid-labeling), a halogen-substituted carboxylic acid amide (e.g., iodoacetamide-labeling) and hydrazine (i.e., by oximation-labeling), it is possible to easily identify the peptide fragment which contained a formylglycine residue and the pep tide fragment which contained a cysteine residue, respectively, in the analyte protein, as corresponding peaks on the chromatograms. It is also possible to determine, semi quantitatively or quantitatively, the ratio between the peptide fragments which contained the cysteine residue and the peptide fragment which contained the formylglycine residue, based on the area of thus identified peaks.

The term "semiquantitative" analysis, regarding the ratio between peptide fragments which contained one of those residues in the analyte protein, herein means a method in which relative evaluation of the levels of corresponding analytical values of an analyte protein lot is made based on comparison with a standard analytical value derived from particular one or more protein lots of: for example, by setting, as a standard, the analytical value or values of particular one or more protein lots, and determining, for another protein lot, the ratio between peptide fragments which contained a cysteine residue and those which contained a formylglycine residue, respectively, in comparison with the standard value. On the other hand, the term "quantitative" analysis means a method in which a protein containing a known amount of cysteine residue and of formylglycine residue, respectively, is labeled and digested; the resulting peptide fragments were analyzed by reverse phase column chromatography; the area of the respective peaks on the chromatogram produced from the peptide fragments are compared with the area of the respective peaks produced from the peptide fragments of an analyte protein; and based on this comparison, the ratio is directly calculated.

In the present invention, the cysteine residue and the formylglycine residue to be analyzed are, in particular, the cysteine residue that has a potential to get converted into a formylglycine residue in the peptide chain of a protein and a formylglycine residue generated by conversion of such a cysteine residue. Because such conversion of a cysteine residue into a formylglycine residue is brought about by a highly specific enzymatic reaction, it is only a particular cysteine residue that can get converted into a formylglycine residue. In the case of sulfuric ester hydrolase, for example, the cysteine residue that can get converted into a formylglycine residue is just the one that is part of the active center.

In the reaction in which a cysteine residue is to get converted into a formylglycine residue, when the cysteine residue has not been fully converted into a formylglycine residue, a mixture will result containing the portion of the protein in which the cysteine residue remains unconverted and the portion of the protein in which the residue has been converted into a formylglycine residue. In this case, analysis of the protein using the method of the present invention allows one to determine, semiquantitatively or quantitatively, the ratio between the protein in which the cysteine residue remains intact and the protein in which the residue has been converted into a formylglycine residue.

When the protein is a sulfuric ester hydrolase, the above analysis is very important. This is because in order for a sulfuric ester hydrolase to exert its enzyme activity, it is essential that a particular cysteine residue located in its active center has been converted into a formylglycine residue. Analysis of a sulfuric ester hydrolase using the method of the present invention enables determination of the ratio of active enzyme, i.e., the enzyme in which the cysteine residue has been converted into a formylglycine residue.

Such analysis of sulfuric ester hydrolase is particularly important when a sulfuric ester hydrolase of interest is that which was produced by recombinant technology. This is because a sulfuric ester hydrolase produced by recombinant technology may be used as a medical drug, and in such cases, it is required from the viewpoint of quality control to find out the ratio of the enzyme that has the enzyme activity.

There are sulfuric ester hydrolases which can be used as medical drugs, namely, iduronate-2-sulfatase, N-acetylgalactosamine-4-sulfatase, N-acetylgalactosamine-6-sulfatase, heparan-N-sulfatase and N-acetyl glucosamine-6-sulfate sulfatase. These can be used in enzyme replacement therapy for patients with Hunter syndrome, Maroteaux-Lamy syndrome, Morquio disease A-type, San Filippo syndrome A-type and D-type, respectively.

Though there is no particular limitation as to analyte proteins in the present invention as far as they contain a formylglycine residue in their peptide chain, preferred are sulfuric ester hydrolases, more preferred are iduronate-2-sulfatase, N-acetylgalactosamine-4-sulfatase, N-acetylgalactosamine-6-sulfatase, heparan-N-sulfatase and N-acetyl glucosamine-6-sulfate sulfatase, and still more preferred is iduronate-2-sulfatase, and these enzymes produced using recombinant technology are particularly preferred.

Regarding each of iduronate-2-sulfatase, N-acetylgalactosamine-4-sulfatase, N-acetylgalactosamine-6-sulfatase, heparan-N-sulfatase and N-acetyl glucosamine-6-sulfate sulfatase, the cysteine residue converted into a formylglycine residue is the cysteine residue (Cys59) located at position 59 from the N-terminus of the mature form of iduronate-2-sulfatase; the cysteine residue (Cys55) located at position 55 from the N-terminus of the mature form of N-acetylgalactosamine-4-sulfatase; the cysteine residue (Cys53) located at position 53 from the N-terminus of the mature form of N-acetylgalactosamine-6-sulfatase; the cysteine residue (Cys50) located at position 50 from the N-terminus of the mature form of heparan-N-sulfatase; and the cysteine residue (Cys55) located at position 55 from the N-terminus of the mature form of N-acetyl glucosamine-6-sulfate sulfatase.

Based on the ratio between the cysteine and the formylglycine residues determined by the analysis according the method of the present invention, it is also possible to set a standard value and establish upon it a standard test for an enzyme prepared using recombinant technology.

EXAMPLES

Though the present invention will be described in further detail below with reference to examples, it is not intended that the present invention be limited to those examples.

[Iodoacetic Acid-Labeling of Human Iduronate-2-sulfatase]

A purified product of recombinant human iduronate-2-sulfatase (rhI2S) was prepared as an analyte according to a known method (U.S. Pat. No. 5,798,239, International Publication WO2012/101998). Namely, 0.1 mg of rhI2S was dissolved in 50 µL of a protein lysis solution (prepared by dissolving 66.8 g of guanidine hydrochloride, 6.1 g of trishydroxymethylaminomethane, and 0.372 g of disodium ethylenediaminetetraacetic acid in water, adjusting the pH to 8.5 with 1N HCl, and then adding water to make 100 mL), and after 4 µL of a reducing solution (prepared by dissolving 10 mg of dithiothreitol in 50 µL of the protein lysis solution) was added and mixed by shaking, the solution was left standing for 30 minutes at room temperature. Four mL of a blocking solution (prepared by dissolving 25 mg of iodoacetic acid in 60 µL of 1N sodium hydroxide) then was added and mixed by shaking, and the solution was left standing in the dark for 30 minutes at room temperature. Then, the resulting reaction product was subjected to gel filtration column chromatography, and the fractions containing rhI2S were collected. This gel filtration column chromatography was conducted by subjecting the reaction product to a Sephadex (trade mark) G-25 superfine (5 mm column diameter, 150 mm column length, GE Healthcare) that had been equilibrated with purified water, and flowing purified water at a flow rate of 1 mL/min at room temperature while monitoring absorbance at a wavelength of 215 nm using an ultraviolet absorption photometer. The rhI2S-containing fraction thus collected was evaporated to dryness under reduced pressure. The resulting product was designated iodoacetic acid-labeled rhI2S.

[Iodoacetamide-Labeling of Human Iduronate-2-sulfatase]

0.1 mg of rhI2S was dissolved in 50 μL of the protein lysis solution (prepared by dissolving in water 66.8 g of guanidine hydrochloride, 6.1 g of trishydroxymethylaminomethane, and 0.372 g of disodium ethylenediaminetetraacetic acid, adjusting the pH to 8.5 with 1N HCl, and then adding water to make 100 mL), and after 4 μL of a reducing solution (prepared by dissolving 10 mg of dithiothreitol in 50 μL of the protein lysis solution) was added and mixed by shaking, the solution was left standing for 30 minutes at room temperature. Four μL of a blocking solution (prepared by dissolving 25 mg of iodoacetamide in 60 μL of 1N sodium hydroxide) was added and mixed by shaking, and the solution was left standing in the dark for 30 minutes at room temperature. Then, the resulting reaction product was subjected to gel filtration column chromatography, and the fractions containing rhI2S were collected. This gel filtration column chromatography was conducted by subjecting the reaction product to a Sephadex (trade mark) G-25 superfine (5 mm column diameter, 150 mm column length, GE Healthcare) that had been equilibrated with purified water, and flowing purified water at a flow rate of 1 mL/min at room temperature while monitoring absorbance at a wavelength of 215 nm using an ultraviolet absorption photometer. The rhI2S-containing fraction thus collected was evaporated to dryness under reduced pressure. The resulting product was designated iodoacetamide-labeled rhI2S.

[DNPH-Labeling]

The iodoacetamide-labeled rhI2S dried under reduced pressure was dissolved in a 2-4-dinitrophenylhydrazine (DNPH) solution (prepared by dissolving 1.3 mg of DNPH hydrochloride (Tokyo Chemical Industry) in 1 mL of 50% acetonitrile-0.5% TFA aqueous solution), the resulting solution was left standing for 1 hour at room temperature, and then evaporated to dryness under reduced pressure. The resulting product was designated as DNPH-labeled rhI2S.

[Trypsin Treatment]

Each of the iodoacetic acid-labeled rhI2S, the iodoacetamide-labelled rhI2S, and iodoacetic acid-DNPH-labeled rhI2S, which had been evaporated to dryness under reduced pressure as mentioned above, was dissolved in 65 μL of purified water, and mixed by shaking after addition of 5 μL of 1 mol/L ammonium bicarbonate aqueous solution. Then, 10 μL of trypsin solution (prepared by dissolving 25 μg of trypsin in 50 mL of 1 mmol/L hydrochloric acid) was added and mixed by shaking, and the mixture was left standing for 9 hours at 2 to 8° C. to allow the reaction to proceed. After the trypsin treatment, trypsin was inactivated by heating for 5 min at 95° C., and the resulting product was designated trypsin-treated product.

[Analysis by Reverse Phase Column Chromatography]

The trypsin-treated product obtained above was, after evaporated to dryness under reduced pressure, dissolved in purified water to make a sample solution, and 30 μL of it was subjected to reversed phase column chromatography for analysis. The reverse phase column chromatography was carried out using a high-performance liquid chromatography apparatus (Shimadzu HPLC LC-20A system), which was fitted with a reverse phase column (Vydac 218TP54, inner diameter: 4.6 mm, length: 250 mm, particle size: 5 μm, Grace Vydac). Solution A, which was an a 0.1% trifluoroacetic acid aqueous solution, and solution B, which was a 0.1% trifluoroacetic acid-70% acetonitrile aqueous solution, were respectively prepared. The reverse phase column was equilibrated with a mobile phase consisting of a mixed solution prepared by mixing solution A and solution B at a ratio [solution A:solution B=98:2 (v/v)], and then each sample solution was applied to the column and chromatography was performed. The proportion of solution B in the mobile phase was linearly increased from 2% to 60% over 46 minutes, and then the proportion of solution B in the mobile phase was linearly increased up to 99% over 7 minutes, and further the mobile phase in which the proportion of solution B was to 99% was allowed to flow through the column for 12 minutes. The flow rate of the mobile phase and column temperature were set to 0.5 mL/min and 50° C., respectively, and a fluorescence detector was installed on the flow path downstream of the column outlet, and absorbance was recorded at 215 nm to produce a chromatogram.

[Results of Analysis]

Comparison of chromatograms of iodoacetic acid-labeled rhI2S and iodoacetamide-labeled rhI2S (the upper and the lower, respectively, in FIG. 1) revealed multiple peaks which did not match between two chromatograms (those peaks indicated by arrows in FIG. 1). They were separately collected and their amino acid sequences were examined. As a result, it was found that all peaks corresponded to peptide fragments which had contained a cysteine residue when in the analyte protein. In particular, peak (1), coming from the iodoacetamide-labeled protein, and peak (2), coming from the iodoacetic acid-labeled protein, were isolated and their amino acid sequences were determined. Both peaks corresponded to a peptide fragment (amino acid sequence: SPNIDQLASHSLLFQNAFAQQAVCAPSR: SEQ ID NO 1) containing the cysteine residue (Cys59) at position 59 from the N-terminus of the mature form of rhI2S, which lacked the signal sequence. As the theory had predicted, peak (2), which corresponded to the peptide derived from the iodoacetic acid-labeled protein, delayed in elution time compared with peak (1), which corresponded to to the peptide derived from the iodoacetamide-labeled protein. Thus, it was confirmed that the peptide fragments which had contained a cysteine residue when in an analyte protein can be identified by comparing the chromatograms produced on the iodoacetic acid-labeled protein and on the iodoacetamide-labeled protein obtained by the present method.

Figure 2:
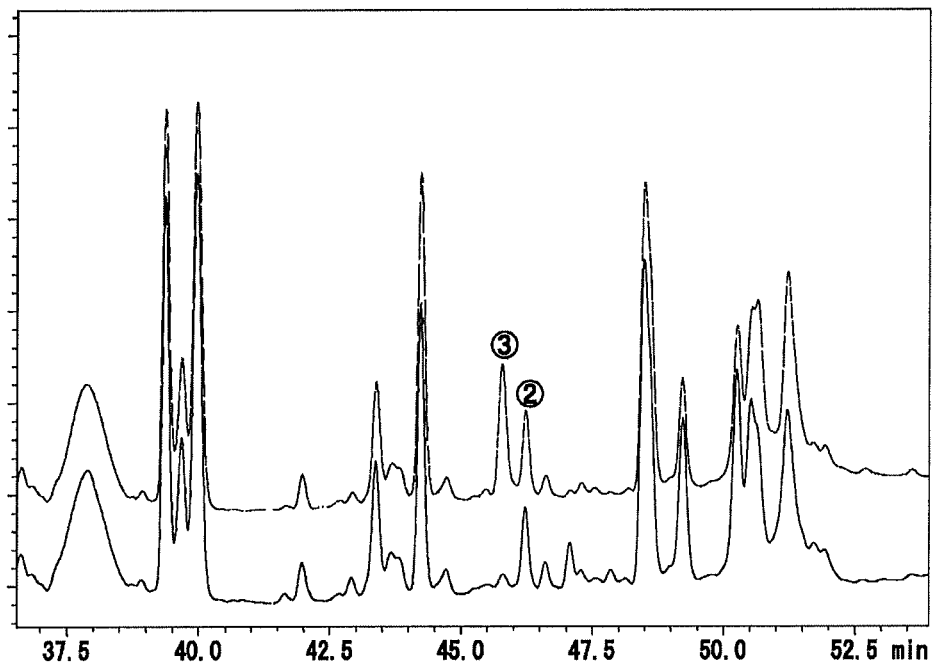
FIG. 2 shows chromatograms obtained as a result of analysis by reverse phase column chromatography of mixtures of peptide fragments prepared by trypsin digestion of iodoacetic acid-labeled rhI2S or and iodoacetic acid-DNPH-labeled rhI2S, respectively, aligned, the one upper and the other lower, with their elution time matched with each other.

Next, focusing on peak (2) in FIG. 1, further analysis was made. Namely, the chromatograms produced on the iodoacetic acid-labeledrhI2S and the iodoacetic acid-DNPH-labeled rhI2S (the upper and lower, respectively, in FIG. 2) were compared. In the chromatogram produced on the iodoacetic acid-DNPH-labeled rhI2S, while peak (2) corresponding to the peptide fragment containing the cysteine residue (Cys59) appeared at the same position as in the chromatogram produced on the iodoacetic acid-labeled rhI2S, peak (3), which had appeared in the chromatogram produced from the iodoacetic acid-labeled rhI2S, was unobserved. The fact that peak (3) appeared when no DNPH labeling was involved while not seen when DNPH-labeling was involved, suggested that peak (3) was a peak to be corresponding to the peptide fragment which had contained a formylglycine residue when in the analyte protein. So, the fraction corresponding to peak (3) appearing in iodoacetic acid-labeled rhI2S was isolated and its amino acid sequence was determined, which confirmed that it corresponded to a peptide fragment in which the cysteine residue which had been located at position 59 (Cys59) from the N-terminus when in the mature form of rhI2S, had been converted into a formylglycine residue (FGly59). As the area of a peak in a chromatogram is substantially proportional to the amount of a corresponding peptide fragment, it was now ascertained that the ratio between the labeled cysteine residue (Cys59) and the formylglycine residue (FGly59) can be determined quantitatively or semiquantitatively by comparing the area of peak (2) and peak (3) appearing in the chromatogram produced on the iodoacetic acid-labeled rhI2S. Meanwhile, as the peak (3) corresponding to the peptide fragment containing the formylglycine residue (FGly59) is supposed to appear at the same position in respective chromatograms produced by analysis of an iodoacetic acid-labeled rhI2S and an iodoacetamide-labeled rhI2S (the upper and the lower in FIG. 1), peak (1) shown in the result of analysis of the iodoacetamide-labeled rhI2S (the lower FIG. 1) consists of overlapping peaks: the one corresponding to the peptide fragment containing the iodoacetamide-labeled cysteine residue (Cys59) and the other corresponding to the peptide fragment containing the formylglycine residue (FGly59) (i.e., peak (3)).

The above results indicate that the peak corresponding to a peptide fragment which contained a cysteine residue when in an analyte protein, can be identified by respectively labeling the analyte protein with iodoacetic acid or iodoacetamide, digesting each product into peptide fragments, subjecting them to reverse phase column chromatography, and then comparing both chromatograms thus produced; that the peptide fragment which contained a formylglycine residue when in the analyte protein, can be identified by respectively labeling the analyte protein with iodoacetic acid or iodoacetic acid-DNPH, digesting each product into peptide fragments, subjecting them to reverse phase column chromatography, and then comparing both chromatograms thus produced; and that the ratio between cysteine and formylglycine residues in the analyte protein can be determined semiquantitatively or quantitatively by comparing the area of the peaks corresponding to the peptide fragment which contained a cysteine residue with the peptide fragment which contained a formylglycine residue.

It is also possible to determine semiquantitatively or quantitatively the ratio between cysteine and formylglycine residues in the protein by labeling an iodoacetamide-labeled protein, instead of an iodoacetic-acid labeled protein, with DNPH, and then analyzing the iodoacetic acid-labeled protein, the iodoacetamide-labeled protein, and the iodoacetamide-labeled-DNPH-labeled protein in the same manner as shown above.

Further, a specification test for rhI2S produced by recombinant technology may be established by setting a standard value upon analysis of a standard compound and calculation of the ratio between its cysteine and formylglycine residues. It is also allowed to set as a standard value the mean of the values obtained from analysis of multiple different lots of a compound.

[3-Iodopropionic Acid-Labeling of Human Iduronate-2-sulfatase]

Analogous to the iodoacetic acid-labeling of human iduronate-2-sulfatase, 3-iodopropionic acid, instead of iodoacetic acid, was used for labeling rhI2S (3-iodopropionic acid-labeling). Further, 3-iodopropionic acid DNPH-labeled rhI2S was obtained by labeling 3-iodopropionic acid-labeled rhI2S with DNPH in the same manner as described above. Then, each of 3-iodopropionic acid-labeled rhI2S, 3-iodopropionic acid-DNPH-labeled rhI2S and iodoacetamide-labeled rhI2S was analyzed by reversed phase column chromatography in the same manner as described above. As a result, it was found that even if 3-iodopropionic acid, instead of iodoacetic acid, was employed for labeling, those peptide fragments can be identified which contained a formylglycine residue when in the analyte protein; and that the ratio between cysteine and formylglycine residues in the analyte protein can be determined, semiquantitatively or quantitatively, by comparing the area of the peak corresponding to a peptide fragment which contained a cysteine residue when in the analyte protein with the area of the peak corresponding to a peptide fragment which contained a formylglycine residue.

[Oximation-Labeling]

Instead of DNPH-labeling, iodoacetic acid-labeled rhI2S was labeled by oximation using O-4-nitrobenzyl hydroxylamine. Oximation-labeling was carried out in the following manner. Namely, iodoacetic acid-labeled rhI2S which had been evaporated to dryness under reduced pressure was dissolved in an O-4-nitrobenzyl hydroxylamine hydrochloride solution [prepared by dissolving 1.3 mg of O-4-nitrobenzyl hydroxylamine hydrochloride (Tokyo Kasei Kogyo) in 1 mL of 50% acetonitrile-0.5% TFA aqueous solution], the resulting solution was left standing for 1 hour at room temperature, and then evaporated to dryness under reduced pressure. The product thus obtained was designated iodoacetic acid-oximation-labeled rhI2S Iodoacetic acid-labeled rhI2S, iodoacetic acid-oximation-labeled rhI2S and iodoacetamide-labeled rhI2S were respectively analyzed in the same method as above using reversed phase column chromatography. As a result, it was found that oximation-labeling using O-4-nitrobenzyl hydroxylamine, instead of DNPH-labeling, also allows identification of the peptide fragments which contained a formylglycine residue when in the analyte protein; and further that the ratio between cysteine and formylglycine residues when in the analyte protein, can be determined, semiquantitatively or quantitatively, by comparing the area of the peaks corresponding to peptide fragments which contained a cysteine residue with the area of the peaks corresponding to peptide fragments which contained a formylglycine residue in the analyte protein.

INDUSTRIAL APPLICABILITY

The present invention enables quantitative or semiquantitative determination of the ratio at which a certain cysteine residue originally present in sulfatase has been converted into a formylglycine residue. Thus, it provides, for example, a method for determination of the proportion of enzymatically active part of a sulfatase produced by recombinant technology, which can be utilized in designing for the optimum manufacturing process of a sulfatase with increased enzymatic activity, and in quality controlling of the products produced by such a process.

The invention claimed is:

1. A method of analysis for a formylglycine residue and a cysteine residue in the amino acid residues that makes up an analyte protein comprising,
    (a) a step of converting the protein respectively into
        (i) a halogen-substituted carboxylic acid-labeled protein by labeling the protein with a halogen-substituted carboxylic acid,
        (ii) a halogen-substituted carboxylic acid amide-labeled protein by labeling the protein with a halogen-substituted carboxylic acid amide, and one of:
        (iii)(a) a halogen-substituted carboxylic acid-hydrazine-labeled protein or a halogen-substituted carboxylic acid-oximation-labeled protein by labeling the protein with a halogen-substituted carboxylic acid and then with hydrazine or by labeling the protein with a halogen-substituted carboxylic acid and then by oximation, or
        (iii)(b) a halogen-substituted carboxylic acid amide-hydrazine-labeled protein or a halogen-substituted carboxylic acid amide-oximation-labeled protein by labeling the protein with a halogen-substituted carboxylic acid amide and then with hydrazine or by labeling the protein with a halogen-substituted carboxylic acid amide and then by oximation;
    wherein the sulfhydryl group of the cysteine residue in the analyte protein is alkylated with the halogen-substituted carboxylic acid or with the halogen-substituted carboxylic acid amide,
    wherein the halogen-substituted carboxylic acid is represented by the following formula (I),

    $$C_mH_{2m}X\text{—COOH} \quad (I)$$

wherein X denotes halogen, and m denotes an integer of 1 to 5, and
    the halogen-substituted carboxylic acid amide is represented by the following formula (II),

    $$C_mH_{2m}X\text{—CONH}_2 \quad (II)$$

wherein X denotes halogen, and m denotes an integer of 1 to 5, and
    wherein the labeling with hydrazine is performed using a hydrazine compound or a salt thereof that forms a hydrazone with the carbonyl group of a formylglycine residue, and
    wherein the labeling by oximation is performed using a hydroxyl amine compound or a salt thereof that forms an oxime group with the carbonyl group of a formylglycine residue,
    (b) a step of digesting each of the labeled proteins to provide a corresponding mixture of peptide fragments,
    (c) a step of subjecting each mixture of peptide fragments to reverse phase chromatography to separate the peptide fragments from each other while monitoring the separated fragments with absorptiometer, producing a chromatogram of the mixture of peptide fragments,
    (d) a step of comparing the produced chromatograms with each other to identify, on the chromatograms, the peak corresponding to a peptide fragment which contained a cysteine residue when in the analyte protein and the peak corresponding to a peptide fragment which contained a formylglycine residue when in the analyte protein.

2. The method according to claim 1, wherein m is an integer of 1 to 3 in formula (I) and formula (II).

3. The method according to claim 1, wherein the halogen is chlorine or iodine in formula (I) and formula (II).

4. The method according to claim 1, wherein the halogen-substituted carboxylic acid is an iodo-substituted monocarboxylic acid or a chloro-substituted monocarboxylic acid; and the halogen-substituted carboxylic acid amide is an iodo-substituted monocarboxylic acid amide or a chloro-substituted monocarboxylic acid.

5. The method according to claim 4, wherein the halogen-substituted monocarboxylic acid is one selected from the group consisting of iodoacetic acid, 2-iodopropionic acid, 3-iodopropionic acid, and chloroacetic acid, and the halogen-substituted carboxylic acid amide is one selected from the group consisting of iodoacetamide, 2-iodopropionic acid amide, 3-iodopropionic acid amide, and chloroacetamide.

6. The method according to claim 4, wherein the halogen-substituted monocarboxylic acid is iodoacetic acid and the halogen-substituted carboxylic acid amide is iodoacetamide.

7. The method according to claim 4, wherein the halogen-substituted monocarboxylic acid is 3-iodo-propionic acid and the halogen-substituted carboxylic acid amide is iodoacetamide.

8. The method according to claim 1, wherein the hydrazine compound or the salt thereof is a 2,4-dinitrophenylhydrazine or a salt thereof, and wherein the hydroxylamine compound or the salt thereof is O-4-nitrobenzyl hydroxylamine or a salt thereof.

9. The method according to claim 1, further comprising a step for determining, on the chromatogram, the ratio of the area of the peak corresponding to the peptide fragment that contained a cysteine residue when in the analyte protein and the area of the peak corresponding to the peptide fragment that contained a formylglycine residue when in the analyte protein.

10. The method according to claim 1, wherein the analyte protein is a human sulfuric ester hydrolase.

11. The method according to claim 10, wherein the sulfuric ester hydrolase is selected from the group consisting of iduronate-2-sulfatase, N-acetylgalactosamine-4-sulfatase, N-acetylgalactosamine-6-sulfatase, heparan-N-sulfatase, and N-acetyl glucosamine-6-sulphate sulfatase.

12. The method according to claim 11, wherein the sulfuric ester hydrolase is iduronate-2-sulfatase.

13. The method according to claim 10, wherein the cysteine residue is that cysteine residue which must have been converted into a formylglycine residue in order for the sulfuric ester hydrolase to exhibit its enzymatic activity, and the formylglycine residue is that formylglycine residue which has been generated by conversion of the cysteine residue.

14. The method according to claim 13, wherein the sulfuric ester hydrolase is iduronate-2-sulfatase, and the cysteine residue and the formylglycine residue are those located at position 59 from the N-terminus of the mature iduronate-2-sulfatase.

15. The method according to claim 14, wherein the iduronate-2-sulfatase is a recombinant iduronate-2-sulfatase.

* * * * *